United States Patent [19]

Hornsby

[11] Patent Number: 5,379,773
[45] Date of Patent: Jan. 10, 1995

[54] ECHOGRAPHIC SUCTION CANNULA AND ELECTRONICS THEREFOR

[76] Inventor: James J. Hornsby, 695 Valley Vista Dr., Camarillo, Calif. 93010

[21] Appl. No.: 124,403

[22] Filed: Sep. 17, 1993

[51] Int. Cl.⁶ ............................................. A61B 8/12
[52] U.S. Cl. ................................. 128/662.06; 604/27
[58] Field of Search .................... 128/662.03, 662.05, 128/662.06, 753, 734, 660.06, 749; 604/27, 28; 607/97

[56] References Cited

U.S. PATENT DOCUMENTS

| | | | |
|---|---|---|---|
| 4,824,434 | 4/1989 | Seitz, Jr. ................................ | 604/27 |
| 5,029,588 | 12/1991 | Yock et al. ....................... | 128/662.06 |
| 5,143,063 | 9/1992 | Fellner ................................ | 607/97 |
| 5,183,052 | 2/1993 | Terwilliger .......................... | 128/753 |
| 5,271,413 | 12/1993 | Dalamagas et al. ................. | 128/734 |

Primary Examiner—George Manuel

[57] ABSTRACT

The Echographic Suction Cannula and Electronics Therefor provides a display of adipose tissue thickness for the Doctor to observe as he moves the cannula within the patient. The cannula includes a piezoelectric transducer which is pulsed by the electronics as a send pulse, to cause ultrasound to penetrate the adipose tissue and provide a reflected receive pulse. A known value fixed frequency source continuously emits cycles, and the electronics counts the cycles emitted between the send and receive pulses. This number is fed to a computer which generates bars equal in height to the thickness and moving across the CRT as the Doctor moves the cannula so he can determine regions where further Liposuction is necessary to even out the patient's appearance.

18 Claims, 9 Drawing Sheets

AVERAGE ADIPOSE DEPTH 31 MM

ECHOGRAPHIC SUCTION CANNULA AND ELECTRONICS THEREFOR

BACKGROUND OF THE INVENTION

This invention relates to an echographic device with a suction cannula and more specifically, to an improved electronically directed medical device for liposuction.

Liposuction is a medical procedure for the aspiration and evacuation of fat from under the skin, and is performed by applying a negative pressure to a cannula, or a plain suction tube, which is moved under the skin surface through a small incision. With the devices currently available for liposuction, pinching of the skin is the only method of estimating the effect of liposuction during treatment on the thickness of fat remaining under the skin. Prior art suction cannulas for liposuction do not provide any means for precisely and continuously monitoring the thickness of the remaining tissue during treatment, and the position of such cannulas within the tissue being treated can be estimated only by palpation. Consequently, surface irregularities and asymmetry were not uncommon, spoiling a large proportion of aesthetic results. This has also led to cannula malpositioning. A cannula, positioned too close to the dermis or to the muscle fascia, may cause surface dimples and furrows. If false passages are made into the deeper vital structure, such as intra-abdominal organs, the consequence of cannula malpositioning can be serious enough to be life-threatening.

Tissue thickness can be measured and displayed by current medical imaging techniques, such as ultrasonography, xeroradiography or magnetic resonance imaging, but their use during liposuction would require interruptions of the operation, and contaminated heavy equipment would have to be brought to the sterile field. Moreover, the equipment would have to be retrieved before the operation can be resumed, and this would have to be repeated any number of times during an operation. As a result, such currently available imaging techniques are seldom used during liposuction and are primarily reserved for pre-operative and post-operative evaluations.

It is therefore a general object of the present invention in view of the above to provide a device including electronic monitoring and display controls and a suction cannula which can make liposuction a safer and more precise procedure and to thereby make it possible to obtain a larger proportion of pleasant aesthetic results.

It is a more specific object of the present invention to provide a device for liposuction which allows continuous, precise monitoring, visual display and recording of the thickness of fatty tissue.

It is another object of the present invention to provide such a device which also allows display and recording to the position of the tissue being treated.

U.S. Pat. No. 5,242,386 entitled ECHOGRAPHICS SUCTION CANNULA, issued Sep. 7, 1993 to Dr. Eric Holzer, and assigned to a common assignee herewith, discloses a preferred cannula for use with the present electronic controls. The disclosure for this patent is incorporated by reference herein.

SUMMARY OF THE INVENTION

A suction cannula, with which the above and other objects can be accomplished, may be characterized as having a handle and a suction tube longitudinally extending therefrom and containing near its tip an ultrasonic transducer. The transducer is partially exposed through a side window so as to be able not only to transmit ultrasonic pulse signals therethrough but also to receive their echoes. The suction tube is provided with suction openings through which fatty tissues are introduced into the tube to be evacuated, the window for the transducer being situated between the tip and these suction openings. A coaxial cable connects the transducer to the external circuit of this invention. The handle has a thumb grip indicative of the angular position of the transducer window with respect to the longitudinal axis of the suction pipe. The position of the cannula within the tissue being treated can be determined by analyzing the time delay between the electric pulse delivered to the transducer and that from the transducer in response to a received echo. The user can have this information displayed as a simultaneous and continuous image during a liposuction treatment.

In the control monitoring and display circuitry, a multi-timer counter receives a clock pulse to initiate a start count to activate a first AND circuit which passes a high frequency burst to the cannula and to a video filter. The start pulse is delayed to set a first flip-flop which enables a second AND circuit which passes a fixed frequency signal with its number of pulses per second being equivalent to the depth of adipose tissue being scanned to a third AND circuit. The effect of the start pulse is delayed again before it reaches the data input of a video filter output flip-flop circuit in order than $Q^*$ (same as Q bar, which means not -Q, the opposite of Q) is high to cause the third AND circuit to pass the fixed frequency signal pulses to an echo counter to begin a count.

The receive pulse from the cannula, engendered by the send pulse passing through the fat tissue and being reflected back to the transducer, causes the video output flip-flop to change state because the further delayed effect of the start pulse has now ended and the data sign, which when clocked into the video flip-flop by the video filter output receive pulse, stops the count in the echo counter by virtue of bringing the third AND circuit low, in order that the now fixed (no longer changing) echo count can be applied to the display via the computer. The data sign at this time also causes the Q output of the video flip-flop to establish a data valid signal at the computer.

At a predetermined count from the multi-timer counter, the first flip-flop is reset, at a further count the video filter flip-flop and echo counter are reset, and at a still further count, the multi-timer counter resets itself.

A simple display algorithm in the computer software insures that sequential display heights are no more or less than 3 mm different from the preceding height.

DETAILED DESCRIPTION OF THE INVENTION

Figure 1:
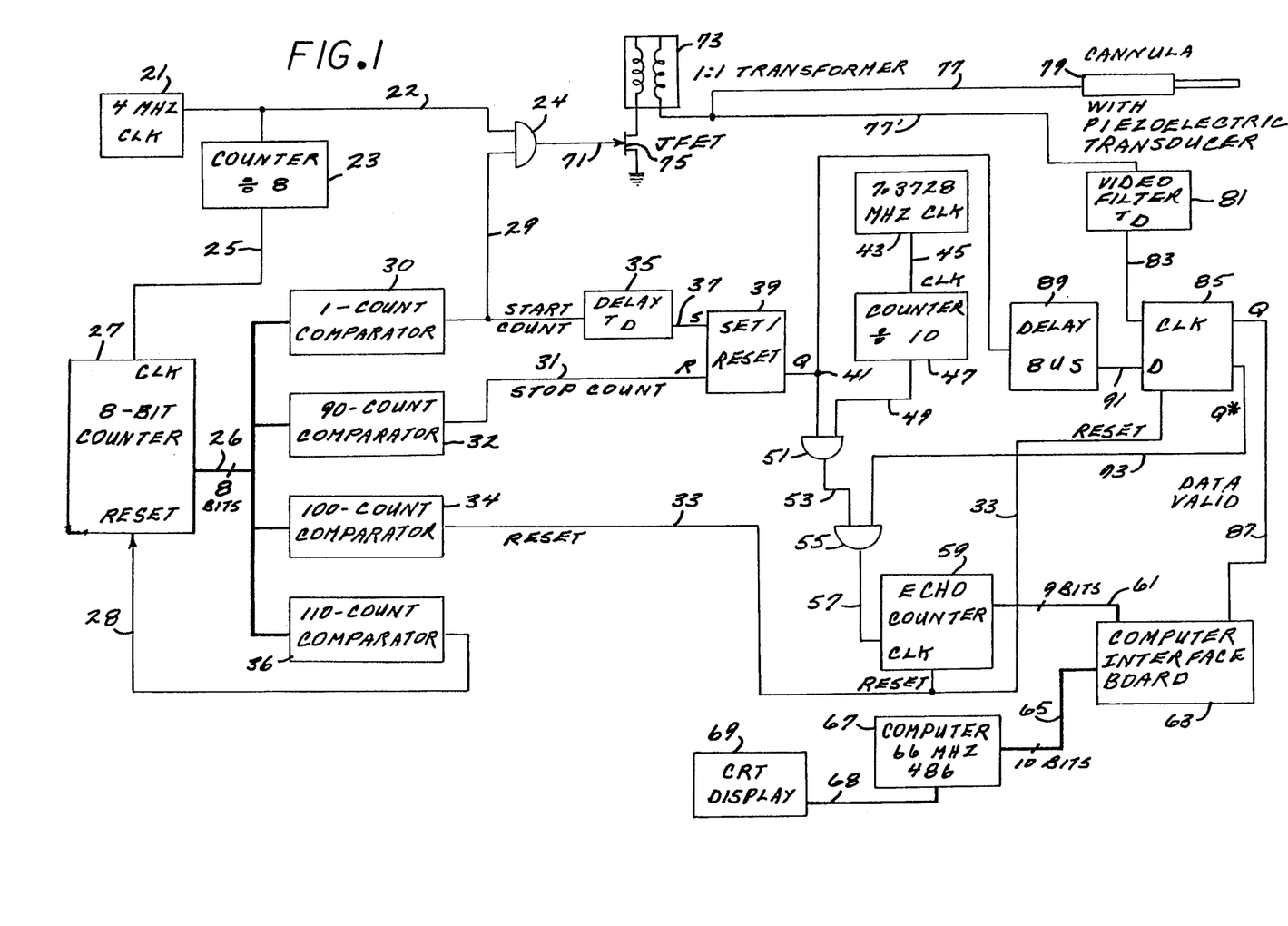
FIG. 1 is a monitoring, display and timing circuit for an echographic suction cannula.
Figures 1A, 1B:
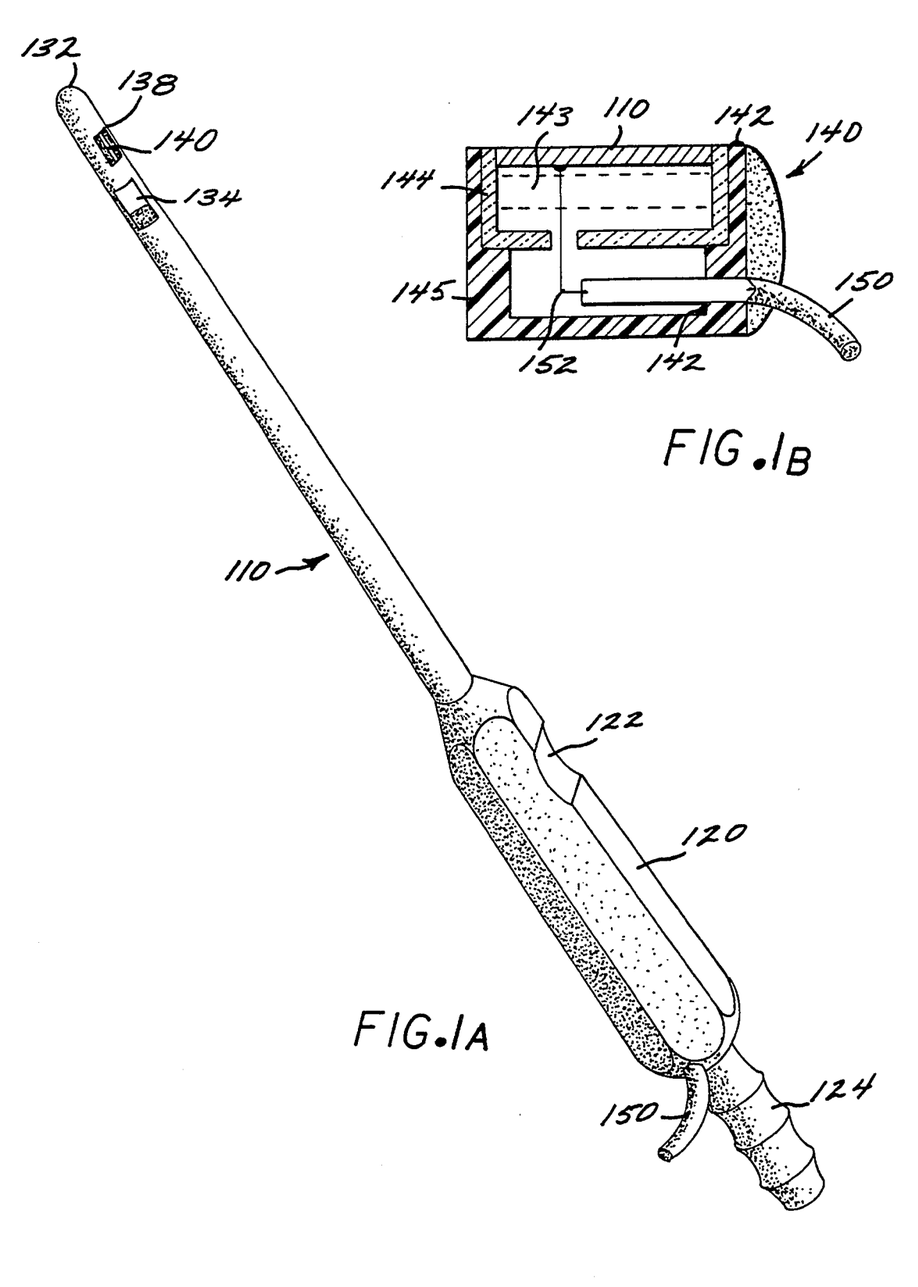
FIG. 1a is a perspective view of the cannula.
FIG. 1b is a cross-sectional view of the transducer in the cannula.

With reference to FIGS. 1a and 1b, an echographic suction cannula 110, according to the present invention may be made of a stainless steel, plastic or carbon material, and consists essentially of a handle 120 at its proximal (to the user's hand) end and a hollow suction tube within outer casing 136 extending forward from the handle 120. The suction tube has a bluntly rounded tip 132 at its forward end, distal from the handle 120, its outer casing 136 having one or more suction openings 134 (only one such opening being visible in FIG. 1a) on its side surface near the cannula tip 132. An ultrasonic transducer assembly 140 (FIG. 1b) is contained within the suction tube, between the cannula tip 132 and the suction opening 134, partially exposed through a window 138 in the casing 136 which provides a 3 degree to 6 degree signal aperture. The assembly 140 is connected to an external electric pulse generating and processing circuit FIG. 2. The handle 120 is provided with a thumb grip 122 at the same angular location as the window 138 for the transducer assembly 140 around the longitudinal axis of the suction tube. The handle 120 is also provided at its back with a tubing grip 124 around the backward extension of the suction tube for making connection to a tubing attached to a vacuum chamber (not shown) serving as a source of negative pressure.

The ultrasonic transducer assembly 140 is situated very close to the suction openings 134. As shown in FIG. 1b, the transducer assembly 140 includes a piezoelectric element 143 connected to a live wire 152 within the coaxial cable 150. Ground terminals 142 are provided, both on the outer surface of the piezoelectric element 143 and within the transducer assembly 140, both connected to the coaxial cable 150. The piezoelectric element 143 is supported by a vibration-buffering backing block, which is itself surrounded by an acoustic insulator 144 and a plastic case 145.

Figure 1C:
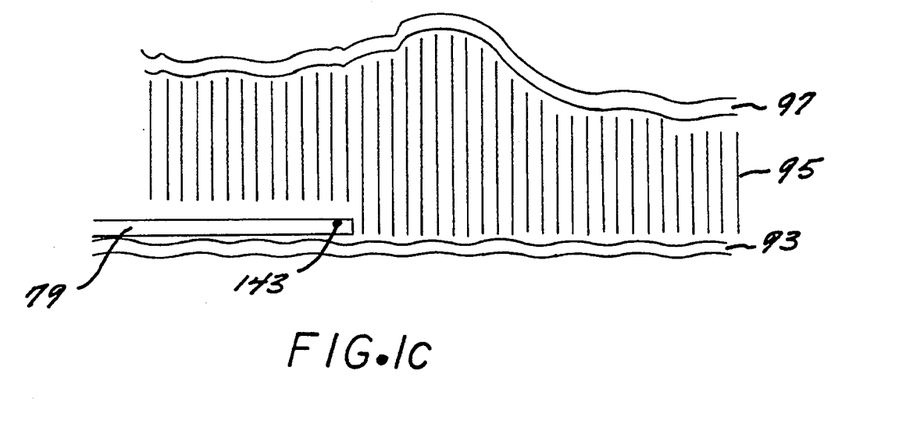
FIG. 1c is a view of the internal adipose, skin, and muscle tissue of a subject with cannula in place.

In FIG. 1c, the cannula 79 is seen inserted into the patient's adipose tissue 95 adjacent to the muscle fascia 93 for emitting ultrasonic pulses from the ultrasonic transducer 143 through the adipose tissue to the inner skin layer, or dermis, 97 and receiving reflected pulses therefrom.

Figure 1D:
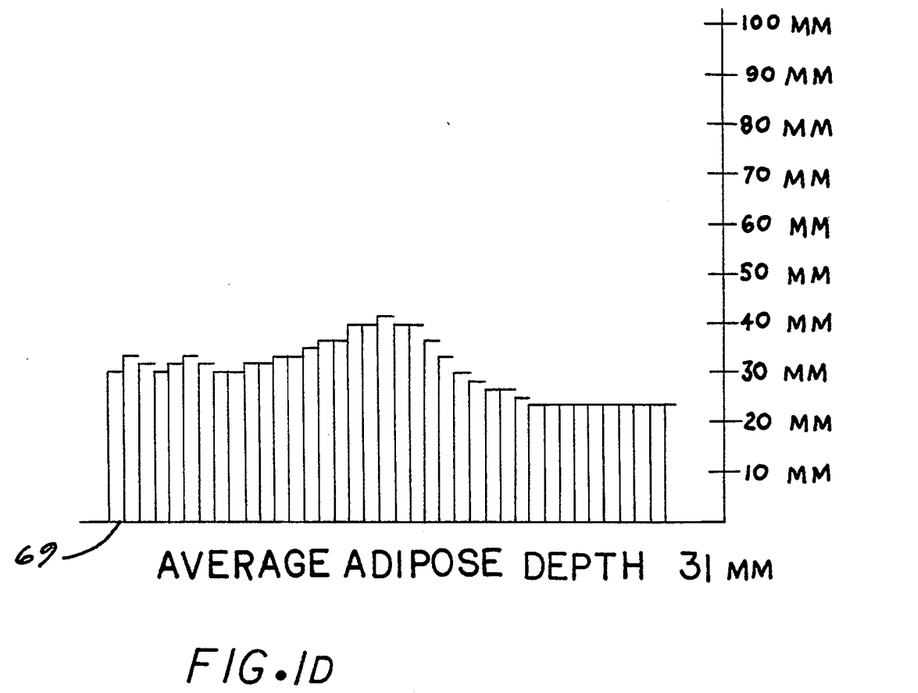
FIG. 1d shows a typical adipose display as detected by the circuit of the present invention.

In FIG. 1d, the display 69 shows the plotted adipose depth to vary between 22 and 44 mm, with an average thickness of 31 mm.

The purpose of the echographic suction cannula device equipped with piezoelectric transducer is to generate a picture graphically of the distance between the suction cannula and the next acoustical interface. This is possible if the physician is moving the cannula with transducer facing upwards towards the skin due to the grip depression on the cannula handle along the muscle layer of a patient on the adipose side (which is standard practice), so that an acoustical wave is reflected off the inner skin layer (dermis) of the patient and back to the transducer. The fat tissue (adipose tissue) in-between the dermis and muscle fascia is echolucent, and will not reflect an acoustical signal if the signal is of sufficiently high frequency.

Thus, the cannula need only send out a sound wave in a tight (preferably 3 to 6 degrees) cone from the transducer and the electronics counts the time required for the first reflected signal to be received. Since the acoustical wave travels at a known velocity in the blood/fat mixture between the dermis and fascia, the distance can be derived by simply counting this time interval.

The resultant display from the cannula and electronics is depicted in FIG. 1c and 1d, which shows the correlation between the adipose tissue "seen" by the transducer (FIG. 1c), and the display seen by the physician (FIG. 1d).

Figure 2:
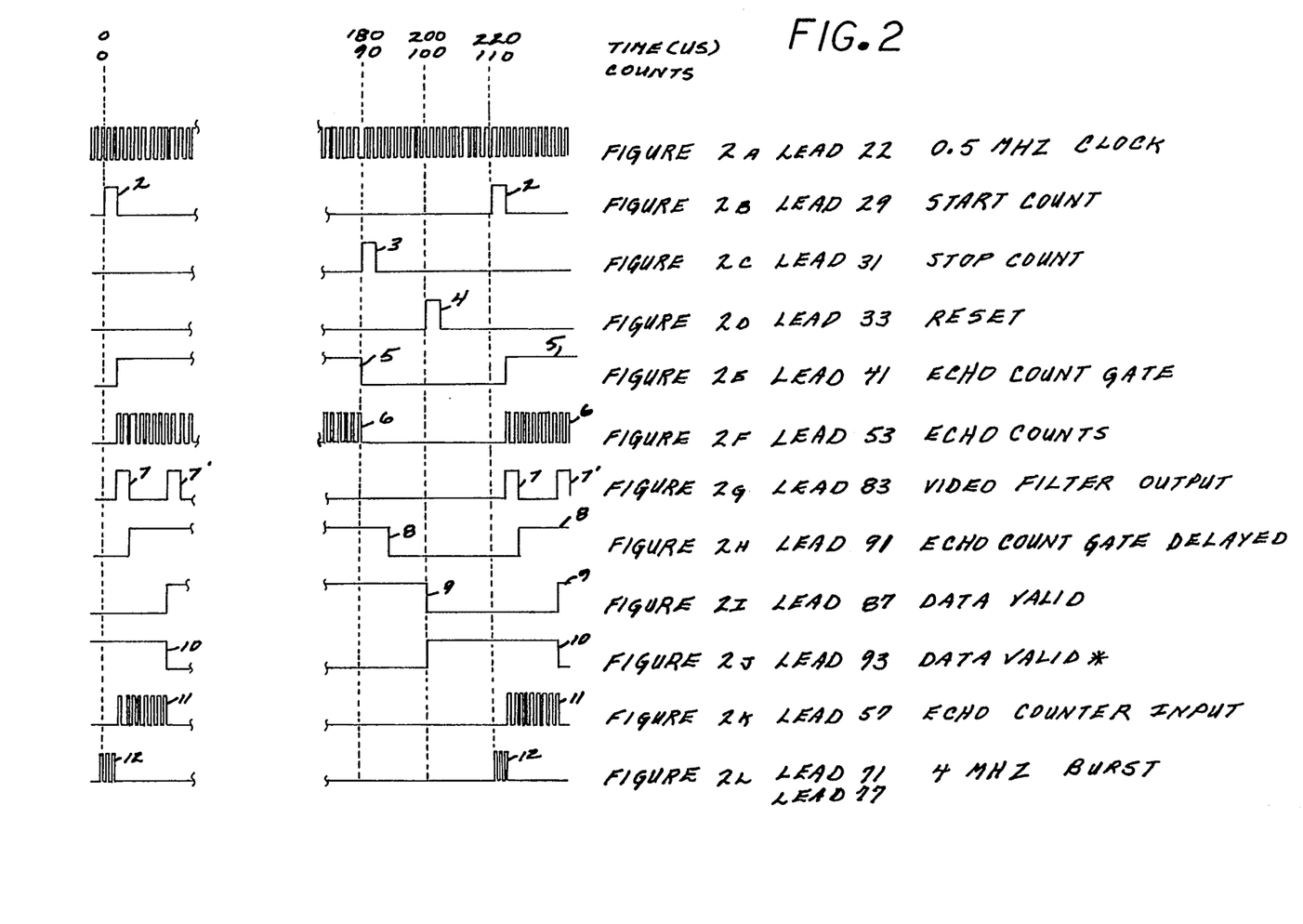
FIG. 2 is a timing waveform display of a dozen different waveforms throughout the circuitry.

Referring now to FIG. 1, the circuit of which is powered by a conventional +/− 12 volt, 5 volt and 35 volt supply (not shown), the 35 volts for Transformer 73, it may be realized that the 4 MHz signal of Block 21 is generated independently from the rest of the circuit of FIG. 1, and is indeed, a conventional crystal in parallel resonance mode in the feedback loop of a CMOS inverter, and runs as long as the power supply is enabled. This clock signal follows Lead 22 to AND Gate 24 and is also routed to the following circuitry: the Divide-By-8 Counter of Block 23 which yields the 0.5 MHz Clock signals, depicted as waveform 1 of FIG. 2a on output Lead 25, which signal is input to the clock of the 8-Bit Counter Block 27. The 8-bit outputs of the Counter Block 27 are input via Lead 26 to the inputs of the 1-Count Comparator (Block 30), 90-Count Comparator (Block 32), 100-Count Comparator (Block 34), and 110-Count Comparator (Block 36). These comparators will output a signal only so long as the input data on Lead 26 matches the specified count of each comparator. Thus the waveform of FIG. 2b shows the Start Count pulse 2 generated by the 1-Count Comparator of Block 30 on Lead 29, which signal is gated with the aforementioned 4 MHz signal at Gate 24 to generate the 4 MHz Burst of signal waveform 12 of FIG. 2l on Lead 71 (FIG. 1). The Start Count 2 (FIG. 2b) not only initiates the 4 MHz Burst at Transformer 73 via Gate 24, but also determines the burst duration at 2 uS, due to the half MHz signal on Lead 25.

Note that the 8-Bit Counter Block 27 is reset by Lead 28 every 110 counts of the clock input on Lead 25 in order to obtain zero counts output on Lead 26. The clock signal of Lead 25 is a 2 microsecond (uS) clock derived from the 4 MHz signal of Lead 22, divided-by-8 at the Divide-by-8-Counter Block 23. Thus, the burst of FIG. 2l, signal waveform 12, is 2 uS long, commencing every 220 uS; since the 110-Count Comparator (Block 36) ensures that the 1-Count Comparator (Block 30) will only see a count of 1 (one) every 110 counts, or 220 uS, which is one cycle of operation for FIG. 1. The cycles will automatically continue as long as the 4 MHz clock is running, which means as long as the power supply is functioning.

The burst signal waveform 12, FIG. 2l, is fed via Lead 71 to the Junction Field-Effect Transistor 75 and thence inverted at the 1:1 isolation Transformer 73, whose output on Lead 77 is fed to the Piezoelectric Transducer 143 of the Echographic Cannula 79. The transducer then sends out the 4 MHz signals, as ultrasound, for 2 uS every 220 uS of waveform 12 of FIG. 2l, which is a burst repetition frequency of 4.545 KHz.

Received echo signals have time to be received from the Start Count of signal waveform 2 of FIG. 2b until the 90-count Stop Count of signal waveform 3 of FIG. 2c; which appears at 180 uS. (See top of FIG. 2.)

The Start Count of Lead 29 is also input to the delay, $T_D$, of Block 35, whose output on Lead 37 is fed to the set input of Flip-Flop Block 39, the delay, $T_D$, of Block 35, is preferably less than 1 uS. The reset input of Block 39 is fed via Lead 31 by the 90-count output of Block 32. The delayed Start Count input to Block 39 on Lead 37 sets the Block 39 Q output on Lead 41, high (HI), while the Stop Count input on Lead 31, after 90 counts, resets the Q output at Lead 41, low (LO), as shown by waveform 5 of FIG. 2e, herein called Echo Count Gate. The Echo Count Gate, or AND Gate 51 is open (HI) for 180 uS minus $T_D$, or 179 uS. (See top of FIG. 2.) When the Q output of Flip-Flop Block 39, on Lead 41, is gated with the standard 7.3728 MHz TTL crystal oscillator signal of Block 43 on Lead 45 divided by the Divide-By-10 Counter of Block 47 and via Lead 49, at AND Gate 51, the Echo Counts 0.73728 MHz clock signal of signal waveform 6, FIG. 2f, Lead 53, is the result. Note that the delay, $T_D$, Block 35, is equal to the delay, $T_D$, of the Video Filter, Block 81, and causes waveform signal 5, of FIG. 2e, Lead Point 41, the Echo Count Gate, to start shortly after the initial Start Count signal 2 of FIG. 2b, Lead 29, so that distance counts start when the 4 MHz Burst signal is received via 77' through the Video Filter Block 81. The Video Filter output on Lead 83, FIG. 2g, furnishes the echo start (waveform 7) and echo received (waveform 7') signals of FIG. 2g.

Since the velocity of the acoustical waves generated by the Piezoelectric Transducer 143 (FIG. 1b) in blood and fat is 1474 meters/second, which yields a velocity of 0.67843 uS/mm, it follows that the maximum allowable distance to send and receive a signal in the allowed time period of 180 uS is 180 uS/1.3569 uS/mm, or 132.6 mm. Clearly, the time periods and counts can be extended for longer (thicker) readings, but 100 mm has been chosen as the maximum depth for the present circuit settings in order to preserve a 0.44 mm maximum error at 100 mm distances, due to the commercial availability of the 7.3728 MHz crystal, which when divided by 10 yields a count period of 1.3563 uS. When this count is used to represent 1 mm the accumulated error at 100 mm is only 0.44 mm, but at 10 mm only 0.044 mm. The signals of waveform 6, FIG. 2f, are the 0.73728 MHz clock signals which are used to derive a one-to-one correspondence between counts and distance.

FIG. 2g shows the pulse 7 on Video Filter output Lead 83, corresponding to the one sent out from the Piezoelectric Element 143, as a result of Burst 12 (FIG. 2l) and the corresponding received pulse 7', with the distance there between being indicative of the amount of adipose tissue between the cannula and the patient's skin.

The Video Filter Output echo stop count signal waveform 7' of FIG. 2g is used at the clock input of flip-flop Block 85 from Lead 83, the output Q* on Lead 93 is waveform signal 10 of FIG. 2j. Since the flip-flop Block 85 data input D on Lead 91, waveform 8 of FIG. 2h, is delayed 8 uS (equivalent to a 6 mm distance) by Delay Block 89 from when Lead 41 feeds signal waveform 5 of FIG. 2e to the input of the Flip-Flop 85.

The first send signal waveform 7 of FIG. 2g from the transducer clocks a LO from the D input of Flip-Flop Block 85 to the Q output register, signal waveform 9 of FIG. 2i, Lead 87, so that Q*, signal waveform 10 of FIG. 2j, Lead 93, is HI, allowing Echo Counts, signal waveform 6 of FIG. 2f, Lead 53, to be gated past Gate 55, inasmuch as the inputs of Gate 55 are Lead 53 and 93; until the receive signal from waveform 7' clocks in a HI from the Delay Block 89, Lead 91, into the D input of Flip-Flop 85, registering the HI on the Q output of Flip-Flop 85, Lead 87. This creates a LO at Q* of Flip-Flop 85 and Gate 55 input, Lead 93, thereby terminating the Echo Counts waveform 6 of FIG. 2f, as shown at signal waveform 11 of FIG. 2k, Lead 57. The Stop Count of waveform 3 of FIG. 2c, Lead 31, at count 90 (180 uS) terminates any Echo Count outputs from Gate 55, Lead 57, by resetting Flip-Flop Block 39, which outputs a LO on Lead 41, which outputs a LO to Gate 51 output, Lead 53, thereby making Gate 55 output, Lead 57, LO, as depicted by Echo Counts waveform 6 of FIG. 2f.

At this time signal waveform 9 of FIG. 2i, is high, and is used as a Data Valid signal, Lead 87. The Echo Counter 59 now has an accurate count of the number of 0.73728 MHz pulses between the Video Filter Output Start and Stop signals (send and receive, waveforms 7 and 7' of FIG. 2g), which is the same number as the number of the measure of the one-way distance from the Cannula to the first echo-reflective surface in millimeters; viz., the muscle fascia 103 to dermis 101, assuming the cannula 79 is at the muscle fascia 130, facing the dermis 101. (Should the reflected signal be received after the Stop Count signal waveform 3, FIG. 2c, interval, Flip-Flop 85 will clock in a LO to Data Valid signal waveform 9, FIG. 2i, so that this count is invalidated, and not registered as a 132 count.) Twenty uS later Reset, signal waveform 4 of FIG. 2d, Lead 33, zeroes the Echo Counter 59 and sets Flip-Flop 85 Q output, Lead 87, Data Valid signal waveform 9, FIG. 2i, LO.

The Echo Counter 59 counts in binary coded decimal, two decimal digits plus a third 1 or 0, to generate up to a 100 count. Therefore, 9 bits are output from the counter. Data Valid signal waveform 9 of FIG. 2i, Lead 87, makes a tenth bit, all of which are interfaced to a 486 computer's local bus, for simple software handling of the data, in order to generate the moving CRT Display of FIG. 4, which is explained in the Display Software section. The data need not be complexed, or even converted, because it is so accurate that the display of FIG. 4 has been simply directly plotted from the data.

VIDEO FILTER

The Video Filter 81 must accomplish three tasks: retrieve a 1.3 mV minimum signal from 5 volts of noise (a signal-to-noise ratio of −72 dB), amplify this signal to TTL levels without adding more noise, and impedance match the filter input to the Piezoelectric Transducer 143. The filter 81 is therefore designed in five stages, the first being passive, the remaining filters being active filters; with clipping diodes D1–D8 to clamp the sending signal, which would otherwise input-saturate the operational amplifiers U1–U4 used and add delay to the filter's recovery time. See FIG. 3. The values for all Video Filter components are set forth in Table I.

Figure 3:
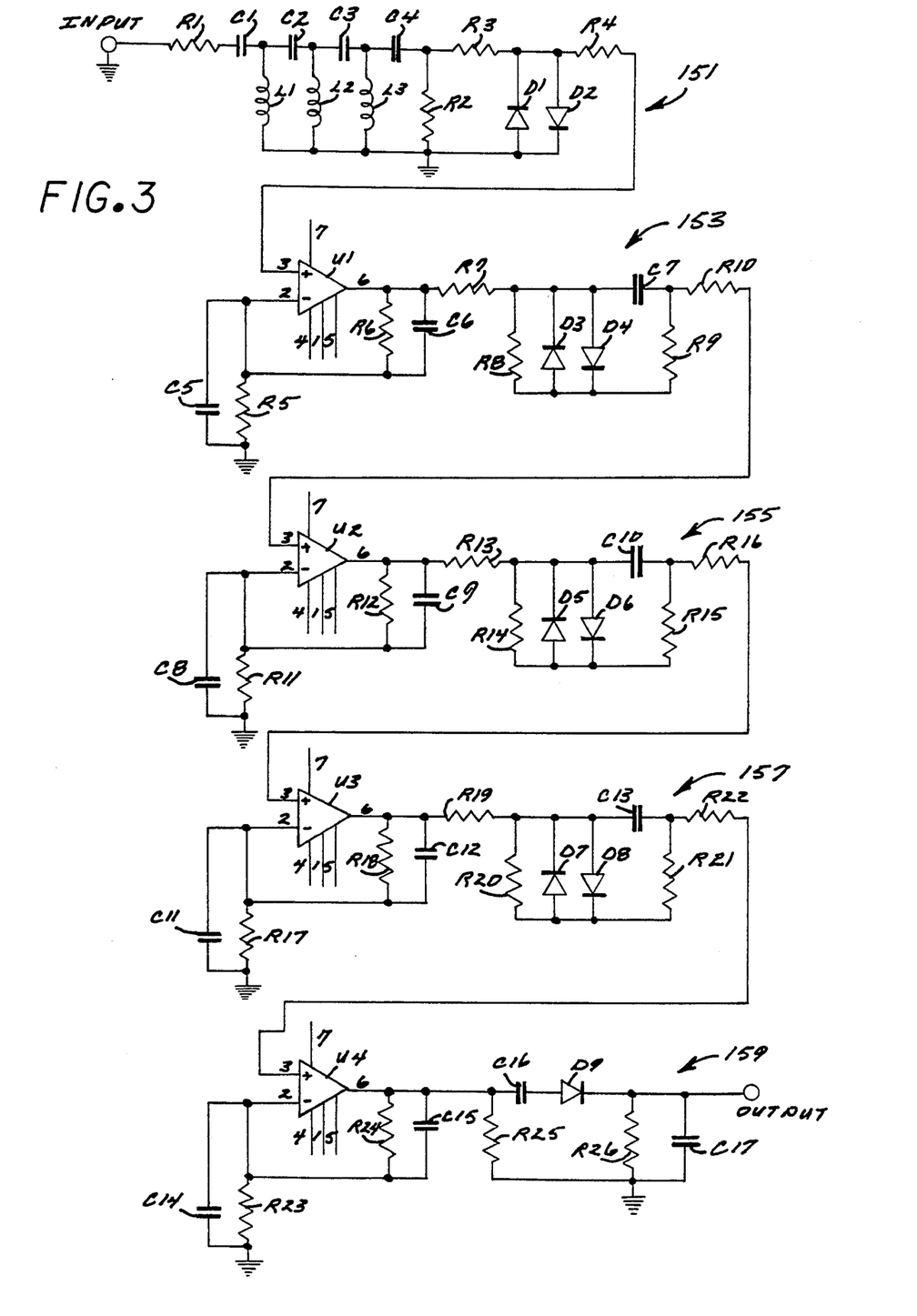
FIG. 3 is a five section video filter unique to the present invention for retrieving the tiny receive signal from video frequency noise.

The first stage 151 is an eighth-order high-pass filter, impedance-matched to the transducer, which has an impedance at resonance (4 MHz) of approximately (50+j0.01)ohms. It is comprised of R1–R3, L1–L3, C1–C4. Clipping diodes D1–D2 are also incorporated. The response of the filter is −13 dB at 4 MHz, −95 dB at 400 KHz. Thus, a 1.3 millivolt signal input at 4 MHz would exit the first stage at 0.26 millivolt, while a 5 volt, 400 Khz signal (a typical undesired ringing frequency in this piezoelectric application) would exit at 0.09 mV.

Figure 5:
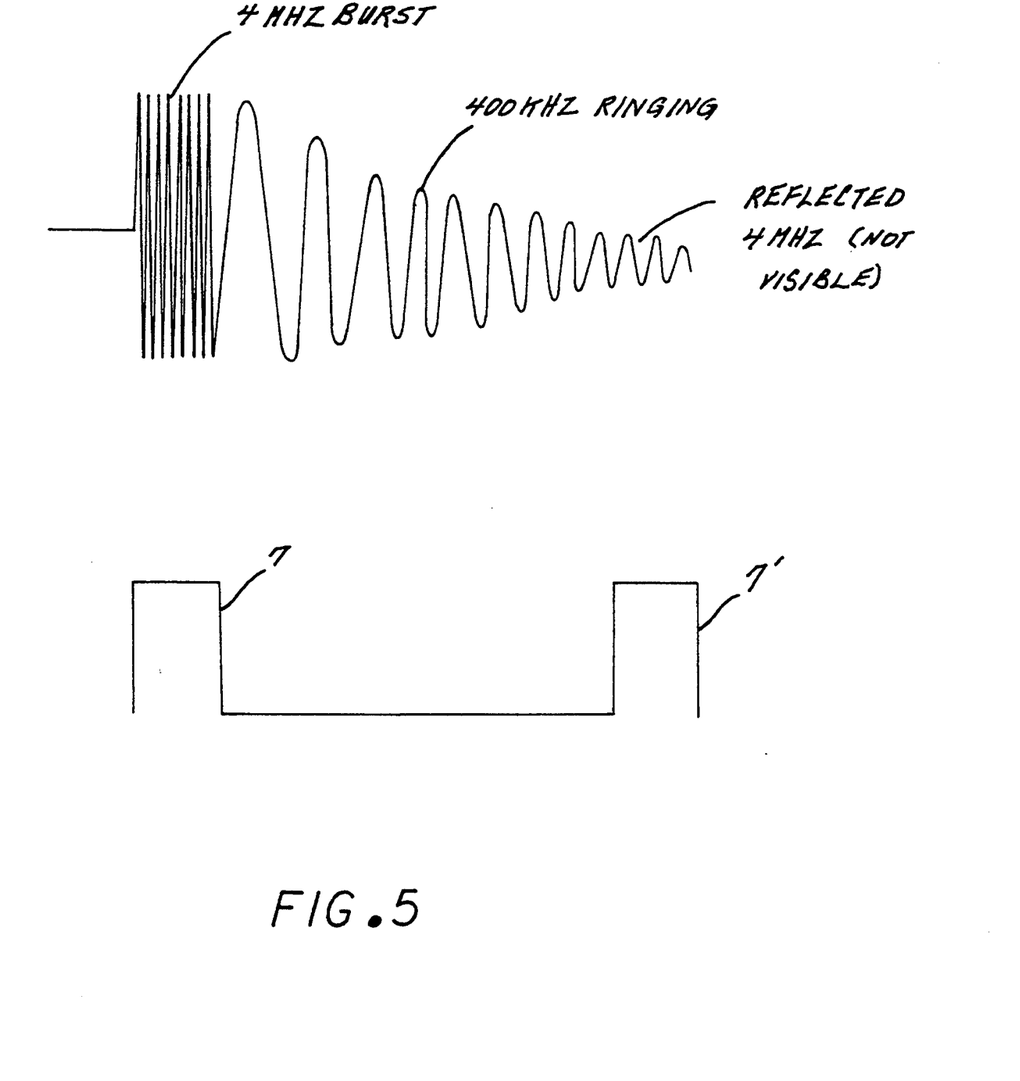
FIG. 5 shows the send pulse with receive noise from which the 4 MHz receive signal is recovered by the video filter.

The remaining stages are AC coupled by capacitors C7 between Stages 153 and 155, C10 between Stages 155 and 157, and C13 between Stages 157 and 159; and clipped by diodes as shown. U1–U4 are the active op-amps used. Both high-pass (C6, R6) and low-pass (C5, R5) filters are incorporated in order to obviate high-frequency oscillations, as well as amplify, to a lesser extent, the lower frequencies. Since R8, R9, and R7 effectively pad the gain of the amp by ⅓ in order to attenuate the send signal further and defeat signal integration, the overall gain of the stage is 4.15 at 4 MHz, and 2.39 at 400 KHz. The gain of the last stage, 159, which does not have an attenuation pad, is 12.4 at 4 MHz, and 7.2 at 400 KHz. Thus, the 1.3 millivolt, 4 MHz signal is amplified to 2.9 V, while the 5 volt, 400 KHz noise is simultaneously attenuated to 0.24 volts! In effect, the video filter has removed video signal at signal-to-noise ratios of −72 dB and converted noise to TTL LO levels, and video to TTL HI levels! FIG. 5 illustrates this function.

DISPLAY SOFTWARE

Figure 4:
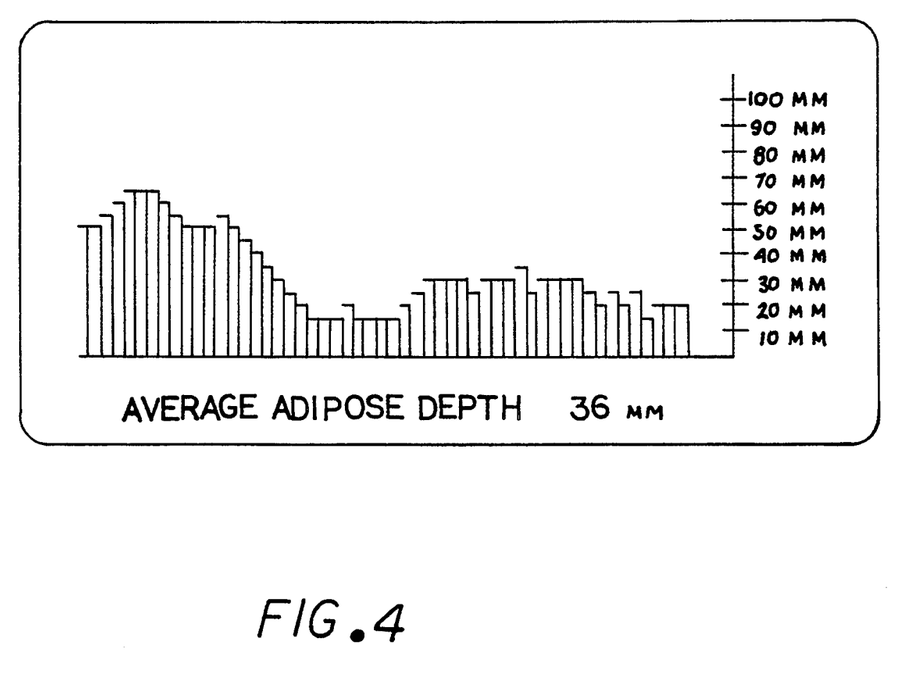
FIG. 4 is a typical chart or CRT display of tissue depth used by the Doctor while moving the cannula within the patient.

The display, as shown in FIG. 4, consists of rightward moving bars, the height being proportional to the data received. The display shows 50 bars at a time, and refreshes from the left, so that the first bar drops off the graph at the right of the screen when the 51st bar appears on the left. The Average Adipose Depth displayed is the running average of each consecutive data point.

The height of the bars is constructed on a per pixel basis to closely approximate 1 mm height per 1 mm depth. Width of the bars is approximately 5 mm. The display incorporates new data with little discernible time lag, unless no Data Valid (9) is received, such as would occur if the cannula is in air or in a deposit greater than 132 mm depth, in which case the bars stop progressing to the right.

The bars move across the screen at a speed predicated by the data rate of 4.545 new data points, or bars per second. Since the data rate is usually slowed because of waiting for data valid signals which are true in order to display new data, this rate of rightward progression of the bars across the display typically varies from 1 to 60 new bars per second, which speed (0.5 cm to 30 cm per second) is not too dissimilar from that of the cannula manipulated by the physician in the patient's body. If the physician holds the cannula steady in the same position within the patient's body, a series of bars all of equal height will appear across the display within a second.

Figure 6:
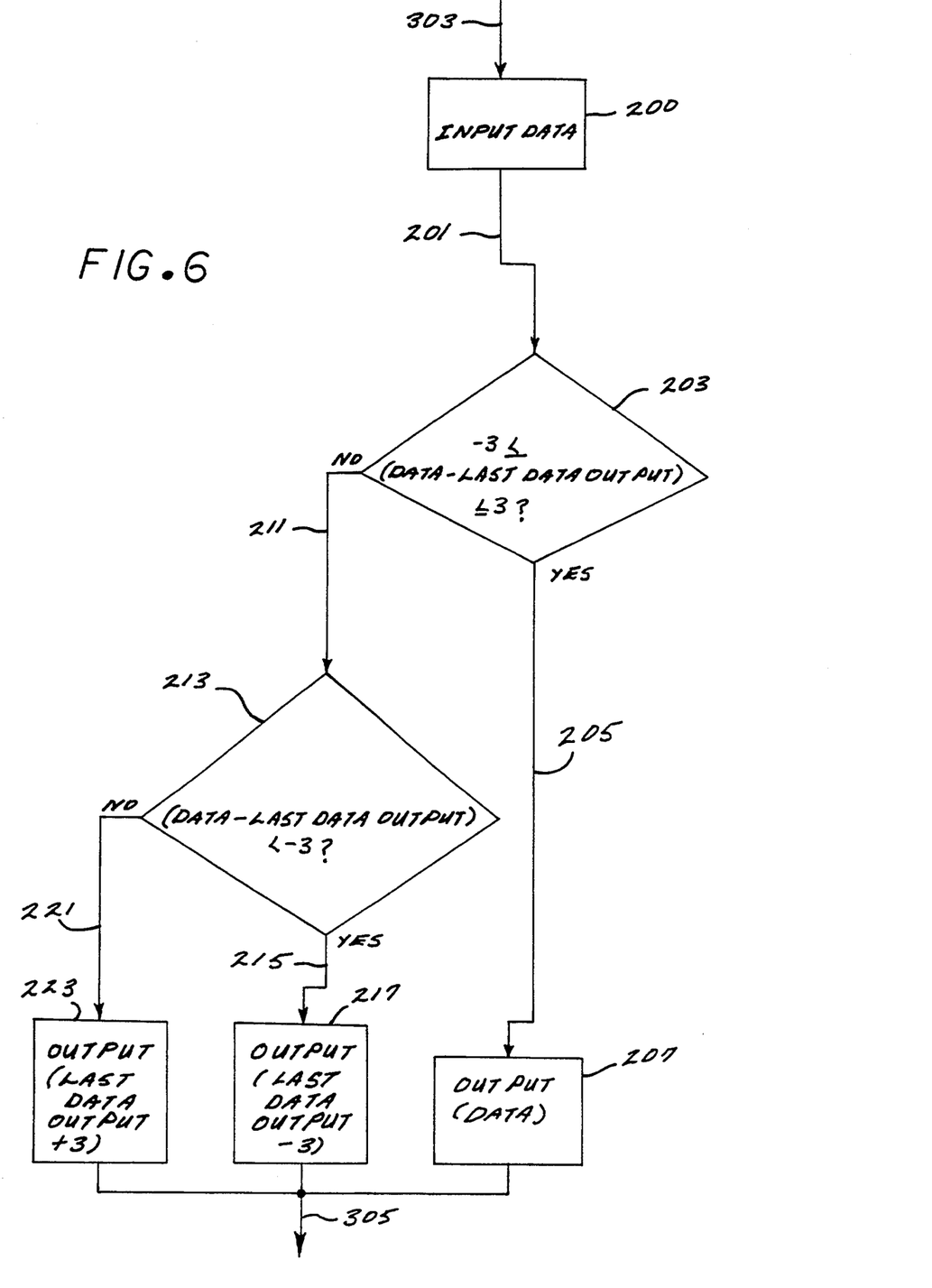
FIG. 6 is a software flowchart for the display filter algorithm.
Figure 7:
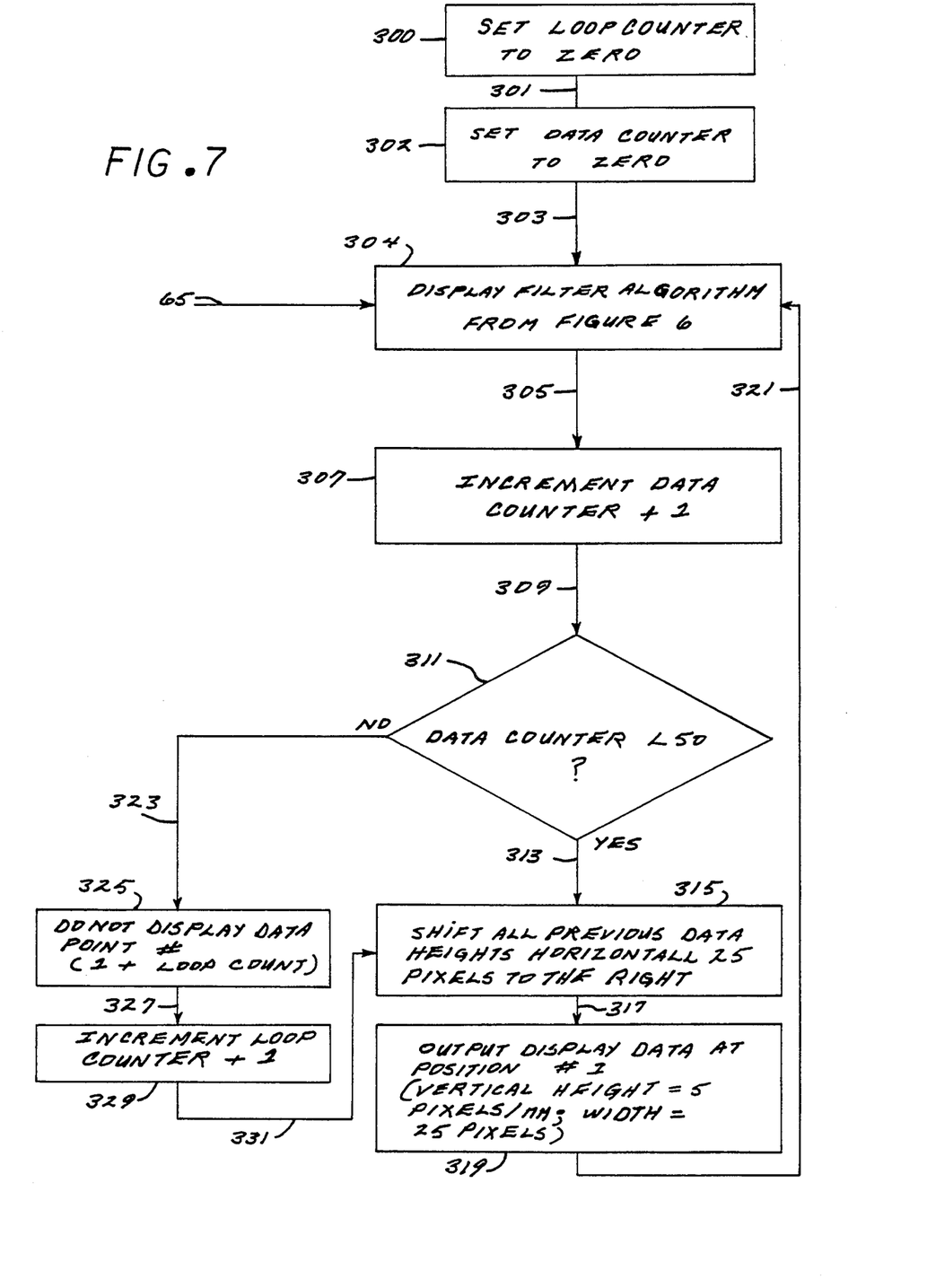
FIG. 7 is a software flowchart for the display frame algorithm.

The simple filtering algorithm of FIG. 6, which is the nested Block 304 of the display frame algorithm, FIG. 7, limits each data point's excursion to a maximum change from the last point of +/− 3 mm. Thus the arbitrary data input points 43 mm, 42 mm, 14 mm, 43 mm, 44 mm; would be displayed as 43 mm, 42 mm, 39 mm, 42 mm, 44 mm. The reason for the smoothing algorithm is to eliminate false low readings which result from the presence of bubbles in front of the transducer. Only objects larger than small bubbles would be extant long enough to allow the filtering algorithm to display radically lower or higher readings with sharp transitions, which do not occur naturally in the body (no right angles). Input data from Input Data Block 200 follows Line 201 to the Decision Block 203, where the decision is made as the whether or not the data point (Data) that Block 203 is now handling is less than or equal to 3 counts difference, either positive or negative, from the previous data point output (Last Data Output). Hence, the single program interrogative of Block 203:

$$-3 \leq (data - last\ data\ output) \leq 3?$$

If the answer is YES, Line 205 is followed to Block 207, which outputs that data point to Line 305.

If the answer to the Block 203 interrogative is NO, Line 211 is followed to the Decision Block 213, which must decide whether the data point is more than 3 counts negative from the previous data. Hence, the single program interrogative of Block 213:

$$(data - last\ data\ output) < -3?$$

If the answer is YES, this means that the data point was more than three counts less than the previous data point, and Line 215 is followed to Block 217, which outputs the previous data point minus 3 counts, instead of the present data point, which is not output, but is discarded. Block 217 outputs the filtered data to Line 305.

If the answer is NO, this means that the data point must have been, by elimination, more than three counts higher than the previous data point, and Line 221 is followed to Block 223, which outputs the previous data point plus 3 counts, instead of the present data point, which is not output, but is discarded. Block 223 outputs the filtered data to Line 305.

The display frame algorithm of FIG. 7 illustrates how the vertical data bars of FIG. 4 are generated. One purpose of the algorithm is to display bars roughly equal in height on the CRT to the mm data count from the output of the filter algorithm (Block 304), and approximately 5 mm in width. For a 1280 pixel×1024 pixel CRT that has a 14 inch (measured diagonally) screen, this translates to 5 pixels/mm, wherein a pixel is a picture element on the CRT. Thus 25 pixels are required horizontally for a 5 mm width, and 200 pixels vertically for a 40 mm data heighth. The other purpose of the algorithm is to display the data as a series of right-ward moving bars, 50 bars at a time, and refreshing the screen from the left, so that the first bar drops off the graph at the right of the screen when the 51st bar appears in the first position on the left.

The algorithm first initiates a program loop counter to zero counts, which is the function of Block 300, then follows Line 301 to Block 302, which sets a data input counter (which counts the number of data points input to the algorithm) to zero. Line 303 is followed from Block 302 to Block 304, which then inputs the first data point from FIG. 6, the filtering nature of which has just been described.

Next, Line 305 leads to Block 307, which increments the data counter by one count. Line 309 following to Decision Block 311, which must decide if the data counter has counted to 50 (fifty) yet. Hence, the interrogative of Block 311:

Data Counter<50?

If the answer is YES, Line 313 leads to Block 315, which will shift all previous data point bars to the right, in order to make room at the leftmost position in FIG.

4 for the new data bar (height), which is the function of Block 319, led to by Line 317. Line 321 allows the algorithm to return to Block 304 for new data.

If the answer is NO, Line 323 leads to block 325, which will cause the data point #1 to not be displayed. Data point #1 by this time has been right-shifted to the right edge of the screen. Line 327 leads to Block 329, which then increments the loop counter by one count, so that the next time Lead 323 is followed, data point #2 is no longer displayed. Lead 331 from Block 329 leads to Block 315, which will again shift all previous data point bars to the right, in order to make room at the leftmost position in FIG. 4 for the new data bar (height), which is the function of Block 319, led to by Line 317. Line 321 allows the algorithm to return to Block 304 for new data. In this manner, all the old points are discarded at the rightmost positions of the display and new ones added at the leftmost positions of the display.

| Item | Quantity | Reference | Part |
|---|---|---|---|
| 1 | 2 | C1,C4 | 1800 PF CAPACITOR |
| 2 | 2 | C2,C3 | 910 PF CAPACITOR |
| 3 | 4 | C5,C8,C11,C14 | 297 PF CAPACITOR |
| 4 | 5 | C6,C9,C12,C15,C17 | 15 PF CAPACITOR |
| 5 | 4 | C7,C10,C13,C16 | .01 UF CAPACITOR |
| 6 | 9 | D1,D2,D3,D4,D5,D6,D7,D8,D9 | 1N4148 DIODE |
| 7 | 2 | L1,L2,L3 | 7.27 UH INDUCTOR |
| 8 | 1 | R1 | 56Ω RESISTOR |
| 9 | 1 | R2 | 91Ω RESISTOR |
| 10 | 5 | R3,R4,R10,R16,R22 | 100Ω RESISTOR |
| 11 | 4 | R5,R11,R17,R23 | 390Ω RESISTOR |
| 12 | 15 | R6,R7,R8,R9,R12,R13,R14,R15,R18,R19,R20,R21,R24,R25,R26 | 2KΩ RESISTOR |
| 13 | 4 | U1,U2,U3,U4 | LM6364 OP-AMP |

What is claimed is:

1. Apparatus for displaying the thickness of adipose tissue between a transducer in a cannula and the patient's dermis, comprising in combination:
a cannula;
a transducer in said cannula;
means for applying periodic spaced-apart bursts of a fixed frequency output to said cannula as send pulses to produce reflected receive pulses by said transducer;
means for producing a further fixed frequency output;
means responsive to said pulses for selecting the number of further fixed frequency cycles occurring during the time interval between said transducer send and said transducer receive pulses to develop a count of said cycles which is an absolute measurement of adipose thickness;
output display means; and,
means for applying said count to the display means to produce a display of bars corresponding in height to the absolute measured thickness of adipose tissue between the cannula transducer and the patient's dermis.

2. Apparatus for displaying the thickness of adipose tissue between a transducer in a cannula and the patient's dermis, comprising in combination:
a cannula;
a transducer in said cannula;
means for applying periodic spaced-apart bursts of a fixed frequency output to said cannula as send pulses to produce reflected receive pulses by said transducer;
means for producing a further fixed frequency output;
means responsive to said pulses for selecting the number of further fixed frequency cycles occurring during the time interval between said transducer send and said transducer receive pulses to develop a count of said cycles which is an absolute measurement of adipose thickness;
output display means;
means for applying said count to the display means to produce a display of bars corresponding in height to the absolute measured thickness of adipose tissue between the cannula transducer and the patient's dermis; and,
said further fixed frequency cycles are selected to provide a one-to-one correspondence between counts and adipose tissue depth is millimeters.

3. The apparatus of claim 2, wherein:
said means responsive to said pulses is a flip-flop clocked by each of said pulses to initiate said count and discontinue said count.

4. The apparatus of claim 3, wherein:
said means responsive to said pulses further comprises a video filter connected between said cannula and said flip-flop to discern and amplify the receive pulses.

5. The apparatus of claim 4, wherein:
said flip-flop provides a data valid signal to said means for applying said count for the display means if the receive pulse is received before a stop count pulse.

6. The apparatus of claim 5, wherein:
said further fixed frequency cycles are 0.73728 MHz to establish one count per millimeter in adipose tissue.

7. Apparatus for displaying the incremental thickness of adipose tissue between a transducer in a cannula and the patient's dermis, comprising in combination:
a cannula;
a transducer in said cannula;
means for producing a fixed frequency output;
means for deriving a start count pulse from the fixed frequency output;
means using the start count to delineate a burst of fixed frequency output;
means applying said burst as a send pulse to the cannula transducer to produce a reflected receive pulse by said transducer;
means for producing a further fixed frequency output;
means responsive to said pulses for selecting the number of further fixed frequency cycles occurring during the time interval between said send and said receive pulses to develop a count of said cycles which is an absolute measure of adipose thickness;
output display means; and,
means for applying said count to the display means to produce a display proportional to the absolute measured thickness of adipose tissue between the cannula transducer and the patent's dermis.

8. Apparatus for displaying the incremental thickness of adipose tissue between a transducer in a cannula and the patient's dermis, comprising in combination:
a cannula;
a transducer in said cannula;

means for producing a fixed frequency output;

means deriving a start count pulse from the fixed frequency output;

means using the start count to delineate a burst of fixed frequency output;

means applying said burst as a send pulse to the cannula transducer to produce a reflected receive pulse by said transducer;

means for producing a further fixed frequency output;

means responsive to said pulses for selecting the number of further fixed frequency cycles occurring during the time interval between said send and said receive pulses to develop a count of said cycles which is an absolute measure of adipose thickness;

output display means;

means for applying said count to the display means to produce a display proportional to the absolute measured thickness of adipose tissue between the cannula transducer and the patient's dermis; and, said means responsive to said pulses is a logical element clocked by each said send and receive pulse, and said start count influences a data input for said element to switch LO and HI outputs, thereby determining the count of said cycles.

9. The apparatus of claim 8, wherein:

said further fixed frequency is selected so that its velocity through the adipose tissue yields a count period of 1.3563 microseconds, which represents 1 millimeter of travel through the tissue.

10. A method of displaying the incremental thickness of adipose tissue between a moving transducer-equipped cannula and the patient's dermis, comprising the steps of:

developing a start count from a fixed frequency clock output pulse;

using the start count to delineate a burst of fixed frequency clock output pulses;

applying said burst to the cannula as a send pulse to develop a reflected receive pulse by the transducer;

using said send and receive pulses to select a number of fixed frequency clock output pulses occurring during the time interval between the send and receive pulses to develop a count which is an absolute measure of adipose tissue thickness; and, applying said count to a computer to produce a moving display of bars corresponding in height to the absolute measured thickness of adipose tissue between the moving cannula and the patient's dermis.

11. A method of energizing a transducer-equipped cannula to develop a display showing height proportional to the thickness of adipose tissue between the cannula and the patient's dermis, comprising the steps of:

applying periodic spaced-apart bursts of a fixed frequency output to said cannula as send pulses to produce reflected receive pulses by said transducer;

providing further fixed frequency output pulses;

counting the number of further fixed frequency output pulses occurring during the time interval between the send and said receive pulses which is an absolute measure of adipose tissue thickness; and, applying the count so obtained to a display means.

12. A method of energizing a transducer-equipped cannula to develop a display showing height proportional to the thickness of adipose tissue between the cannula and the patient's dermis comprising the steps of:

applying periodic spaced-apart burst of a fixed frequency output to said cannula as send pulses to produce reflected receive pulses by said transducer;

providing further fixed frequency output pulses;

counting the number of further fixed frequency output pulses occurring during the time interval between said send and said receive pulses which is an absolute measure of adipose tissue thickness;

applying the count so obtained to a display means; and, extracting a timing start count from said fixed frequency output pulses; and, using said start count to extract said bursts from said fixed frequency output pulses.

13. The method of claim 12, comprising the further step of:

selecting the frequency of said further fixed frequency output pulses so that its velocity through the adipose tissue yields a count period having a one-to-one relationship with travel distance through the tissue in millimeters.

14. The method of limiting data point excursion to a maximum change from the last data of plus or minus 3 millimeters for display in a liposuction system wherein a piezoelectric transducer-equipped cannula receives a burst of energy as a send pulse which causes a reflected pulse from the dermis of the patient to pass through several millimeters of adipose tissue such that the send and receive pulses can define a number of cycles of fixed frequency in the time interval there between to serve as data proportional in height to the thickness of the adipose tissue, comprising the steps of:

determining if the data point under consideration is less than or equal to three counts from the previous data point;

directly outputting the data point if it is less than or equal to three counts difference;

when the data point is not less than or equal to three counts difference, determining if the data point is more than three counts negative from the previous data point;

when the data point is more than three counts negative from the previous data point; output the previous data point less three millimeters instead of the data point under consideration, which is discarded;

permitting a new data point for consideration each time the previous data under consideration is output;

when the data point is not more than three counts negative from the previous data point and not within plus or minus three counts of the previous data point, output the previous data point plus three millimeters and discard the data point under consideration; and, permitting a new data point for consideration each time the data under consideration is discarded.

15. Apparatus for displaying the thickness of adipose tissue in a patient, comprising in combination:

a cannula having a piezoelectric transducer for insertion into a patient's body with the cannula disposed between the muscle fascia and the dermis, and the transducer being open to reflected ultrasound waves from the dermis;

means applying periodic spaced-apart bursts of a fixed frequency output to said transducer as send pulses to produce said reflected receive pulses from the transducer;

means for producing a further fixed frequency output;

means responsive to said pulses for selecting the number of fixed frequency cycles occurring during the time interval between said send and said receive pulses to develop a count of said cycles which is an absolute measure of adipose tissue thickness;

computer means with output display; and, terminals whereat said computer means with output display may be connected to receive the counts as input information and show height proportional to adipose tissue absolute thickness between the transducer and said dermis.

16. Apparatus for displaying the incremental thickness of adipose tissue in a patient, comprising in combination:

a cannula having a piezoelectric transducer for insertion into a patient's body with the cannula disposed between the muscle fascia and the dermis, and the transducer being open to reflected ultrasound waves from the dermis;

means for producing a fixed frequency output;

means for deriving a start count pulse from the fixed frequency output;

means for using the start count to delineate a burst of fixed frequency output;

means for applying said burst as a send pulse to the cannula to produce a reflected receive pulse by said transducer;

means for producing a further fixed frequency output;

means responsive to said pulses for selecting the number of further fixed frequency cycles occurring during the time interval between said send and said receive pulses to develop a count of said cycles which is an absolute measure of adipose tissue thickness;

terminals whereat a computer means with output display may be connected to receive said count; and, means for applying said count to said computer means with output display to produce a display outline corresponding in height to the absolute thickness of adipose tissue between the cannula and the patient's dermis.

17. Apparatus for developing burst pulses to energize a piezoelectric transducer of a cannula adapted to be placed within the patient's body, against a muscle fascia, to direct ultrasonic energy across the adipose tissue between the cannula and the dermis of the patient pursuant to the burst pulses and receive reflected receive pulses from the dermis, comprising in combination:

a clock of fixed frequency cycles so that the velocity of the fixed frequency cycles through the adipose tissue yields a count period having a one-to-one relationship with travel distance through the tissue in millimeters;

timing means for extracting a start count from said clock; and, means using said start count to extract said burst from said fixed frequency.

18. Apparatus for developing burst pulses to energize a piezoelectric transducer of a cannula adapted to be placed within the patient's body, against a muscle fascia, to direct ultrasonic energy across the adipose tissue between the cannula and the dermis of the patient pursuant to the burst pulses and receive reflected receive pulses from the dermis, comprising in combination:

a clock of fixed frequency cycles so that the velocity of the fixed frequency cycles through the adipose tissue yields a count period having a one-to-one relationship with travel distance through the tissue in millimeters;

timing means for extracting a start count from said clock;

means using said start count to extract said bursts from said fixed frequency;

said clock frequency is 4 megahertz and said start count is derived from the 4 megahertz by the timing means dividing by 8 to produce a 2 microsecond start count; and, said means using the start count comprises an AND circuit with one input being the start count and the other input being the clock frequency, whereby said bursts of 4 megacycles are 2 microsecond bursts.

* * * * *